US009433340B2

(12) United States Patent
Jones et al.

(10) Patent No.: US 9,433,340 B2
(45) Date of Patent: Sep. 6, 2016

(54) SYSTEM AND METHOD FOR RAPID SHUTTLING OF TOOLS THROUGH ENDOSCOPES

(71) Applicant: Endoscopic Innovations LLC, Omaha, NE (US)

(72) Inventors: Michael B. Jones, Omaha, NE (US); Carl Nelson, Lincoln, NE (US)

(73) Assignee: ENDOSCOPIC INNOVATIONS LLC, Omaha, NE (US)

(*) Notice: Subject to any disclaimer, the term of this patent is extended or adjusted under 35 U.S.C. 154(b) by 0 days.

(21) Appl. No.: 14/693,337

(22) Filed: Apr. 22, 2015

(65) Prior Publication Data

US 2015/0342445 A1    Dec. 3, 2015

Related U.S. Application Data

(60) Provisional application No. 62/005,555, filed on May 30, 2014.

(51) Int. Cl.
| | |
|---|---|
| *A61B 1/00* | (2006.01) |
| *A61B 1/018* | (2006.01) |
| *A61B 10/04* | (2006.01) |
| *A61B 10/06* | (2006.01) |
| *A61B 1/04* | (2006.01) |
| *A61B 10/02* | (2006.01) |
| *A61B 17/00* | (2006.01) |

(52) U.S. Cl.
CPC .......... *A61B 1/00133* (2013.01); *A61B 1/018* (2013.01); *A61B 10/04* (2013.01); *A61B 10/06* (2013.01); *A61B 2010/0208* (2013.01); *A61B 2010/0225* (2013.01); *A61B 2017/0034* (2013.01)

(58) Field of Classification Search
CPC .......... A61B 1/00121; A61B 1/00128; A61B 1/00133; A61B 1/018; A61B 1/00105; A61B 1/31; A61B 1/00087; A61B 10/04; A61B 10/06
USPC ................ 600/104, 106, 562, 118, 153–159; 606/205
See application file for complete search history.

(56) References Cited

U.S. PATENT DOCUMENTS

| | | |
|---|---|---|
| 5,240,011 A | 8/1993 | Assa |
| 5,431,645 A | 7/1995 | Smith et al. |
| 5,762,069 A | 6/1998 | Kelleher et al. |
| 5,775,333 A | 7/1998 | Burbank et al. |
| 6,249,713 B1 | 6/2001 | Geiger et al. |
| 6,626,850 B1 | 9/2003 | Chau et al. |
| 7,226,424 B2 | 6/2007 | Ritchart et al. |
| 7,727,185 B2 | 6/2010 | Weitzner et al. |

(Continued)

FOREIGN PATENT DOCUMENTS

JP     2000000207 A    1/2000

*Primary Examiner* — Timothy J Neal
(74) *Attorney, Agent, or Firm* — Hackler Daghighian Martino & Novak (57) ABSTRACT

A device for quickly advancing/retracting a biopsy tool (or other driven object) into position through a colonoscope or other such scope. The device includes a drive actuator, a transmission for coupling the actuator to a driven object (biopsy tool), an attachment assembly that couples the device to the endoscope, such as to a biopsy port on the endoscope, an electronic control unit, and a user interface. Preferably, the driver/biopsy tool coupling consists of a motor and a combination of gears and friction rollers.

28 Claims, 7 Drawing Sheets

(56) References Cited

U.S. PATENT DOCUMENTS

| | | | |
|---|---|---|---|
| 8,002,696 B2* | 8/2011 | Suzuki | A61B 1/00133 600/104 |
| 8,025,627 B2 | 9/2011 | Freeman | |
| 8,105,230 B2 | 1/2012 | Honda et al. | |
| 8,177,709 B2 | 5/2012 | Uchiyama et al. | |
| 8,221,308 B2 | 7/2012 | Noguchi et al. | |
| 8,414,505 B1 | 4/2013 | Weitzner et al. | |
| 8,512,227 B2 | 8/2013 | Murakami et al. | |
| 2004/0106853 A1 | 6/2004 | Moriyama | |
| 2005/0222494 A1 | 10/2005 | Prescott | |
| 2005/0272976 A1* | 12/2005 | Tanaka | A61B 1/00073 600/114 |
| 2006/0243285 A1 | 11/2006 | Small | |
| 2007/0299305 A1* | 12/2007 | Murakami | A61B 1/018 600/106 |
| 2009/0287111 A1* | 11/2009 | Kaye | A61B 1/012 600/562 |
| 2013/0225925 A1 | 8/2013 | Kang | |

* cited by examiner

SYSTEM AND METHOD FOR RAPID SHUTTLING OF TOOLS THROUGH ENDOSCOPES

RELATED APPLICATIONS

The present application claims priority from U.S. Provisional Ser. No. 62/005,555, filed May 30, 2014.

FIELD OF THE INVENTION

This invention relates to systems and methods that facilitate the removal of multiple tissue samples and, more particularly, to a system for rapidly advancing and retracting biopsy forceps multiple times through an endoscope, e.g., a colonoscope, ureteroscope, or gastroscope.

BACKGROUND

It is often desirable and frequently necessary to sample or test a portion of tissue, particularly in the diagnosis and treatment of patients with cancerous tumors, pre-malignant conditions, and other diseases or disorders. Biopsy may be done by open, minimally-invasive, or percutaneous techniques. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an artificial imaging device, and may be either a fine needle aspiration (FNA) or a core biopsy. A minimally invasive procedure is performed by passing a sampling device through an endoscope or similar instrument such as a colonoscope or a ureteroscope.

Figure 1:
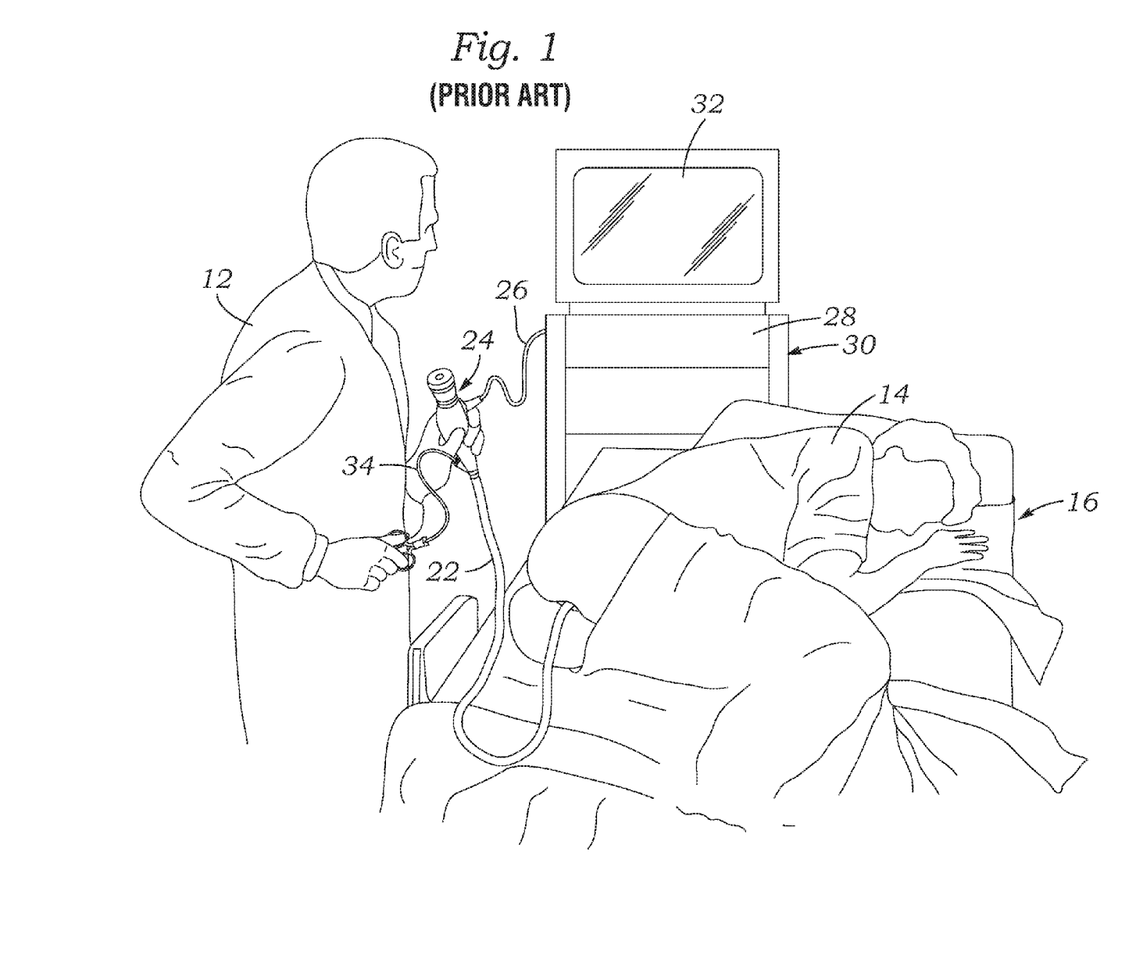
FIG. 1 illustrates a patient undergoing a colonoscopy performed by a physician using a colonoscope and a biopsy forceps.

Referring now to FIG. 1, a colonoscopy is shown wherein a physician 12, or endoscopist, performs a colonoscopy or other endoscopic procedure on a patient 14. During the procedure, the patient 14 is anesthetized while lying on a bed, cart, or stretcher 16. The patient 14 typically lies on his or her side, as shown. To perform a colonoscopy the physician 12 inserts a flexible tube 22 of a fiberoptic flexible colonoscope 24 through the rectum into the patient's colon. The flexible tube 22 usually contains a fiberoptic cable, an air line for inflating the colon, and a light for examining the mucosa therein. A communication cable 26 is coupled to medical equipment 28 supported by an equipment cart 30. The medical equipment 28 includes signal processing equipment and other control devices for supplying the camera signal to a video monitor 32. The cable 26 may also provide an avenue for passage of the air line for use in insufflation of the colon.

Figure 2:
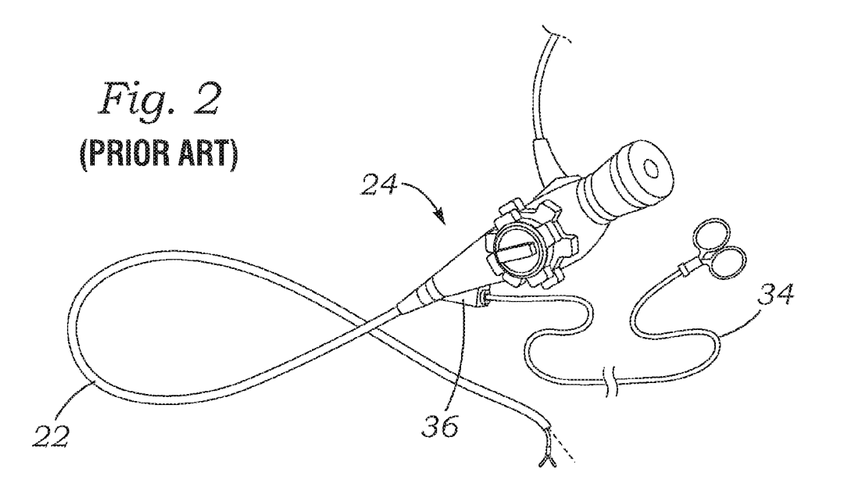
FIG. 2 is a perspective view of the colonoscope and biopsy forceps inserted into a side port.
Figure 3:
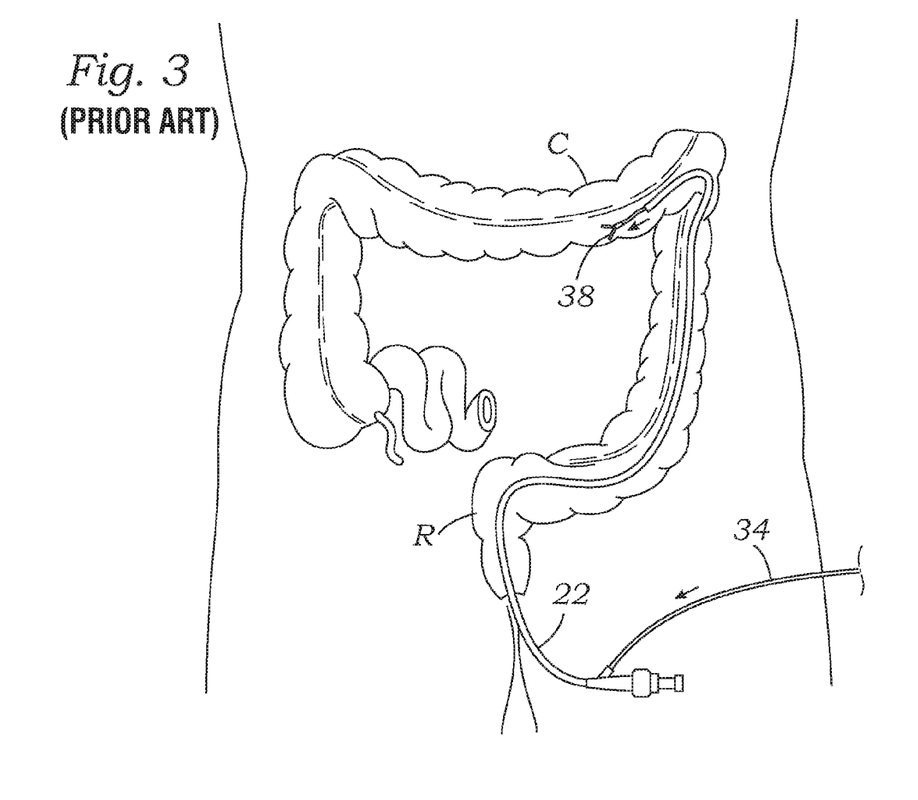
FIG. 3 is a schematic view of the colonoscope and biopsy forceps inserted therethrough within the patient's colon.

Also with reference to FIGS. 2-3, the doctor examines the entire length of the rectum B and colon C with the colonoscope 24. Special instruments such as elongated forceps 34 can be passed through a side port 36 in the colonoscope 24 to biopsy (sample) or remove any suspicious-looking areas such as polyps, if needed. For example, FIG. 3 shows a distal end effector or grabber 38 of the forceps 34 projecting from within the flexible tube 22.

Figure 4A:
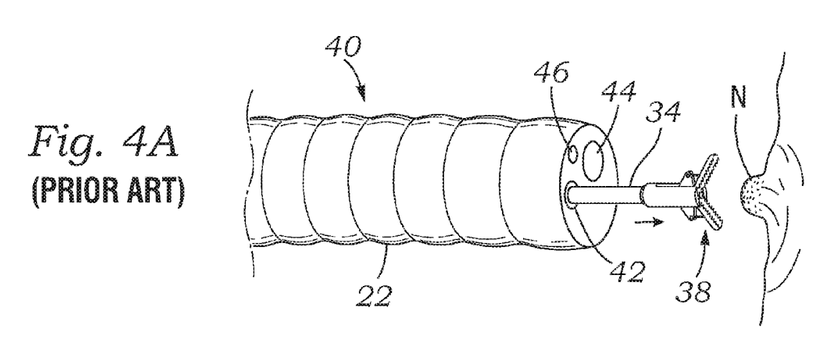
FIGS. 4A and 4B are perspective views of the distal end of the colonoscope showing a distal grabber of the forceps being used to resect a suspicious looking nodule.
Figure 4B:
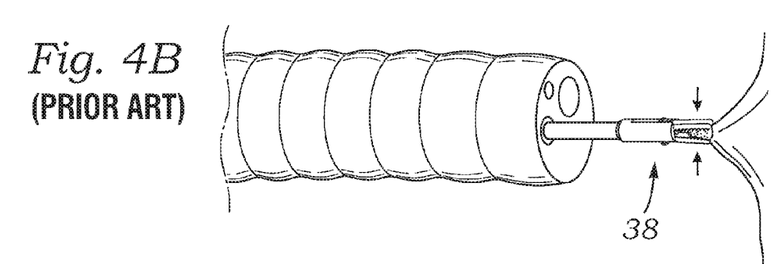

As seen in FIGS. 4A and 4B, a distal end 40 of the colonoscope tube 22 includes a port 42 from which the distal grabber 38 of the forceps 34 emerges. A lens 44 provides the terminus of the fiberoptic cable, and a second open port 46 enables insufflation and expansion of the area. When the physician identifies a suspicious-looking area, such as the nodule N, he or she extends the distal grabber 38 and closes its jaws. The jaws are designed to resect and capture the nodule N, and the physician then can retract the grabber 38 proximally through the entire colonoscope tube 22.

Figure 5:
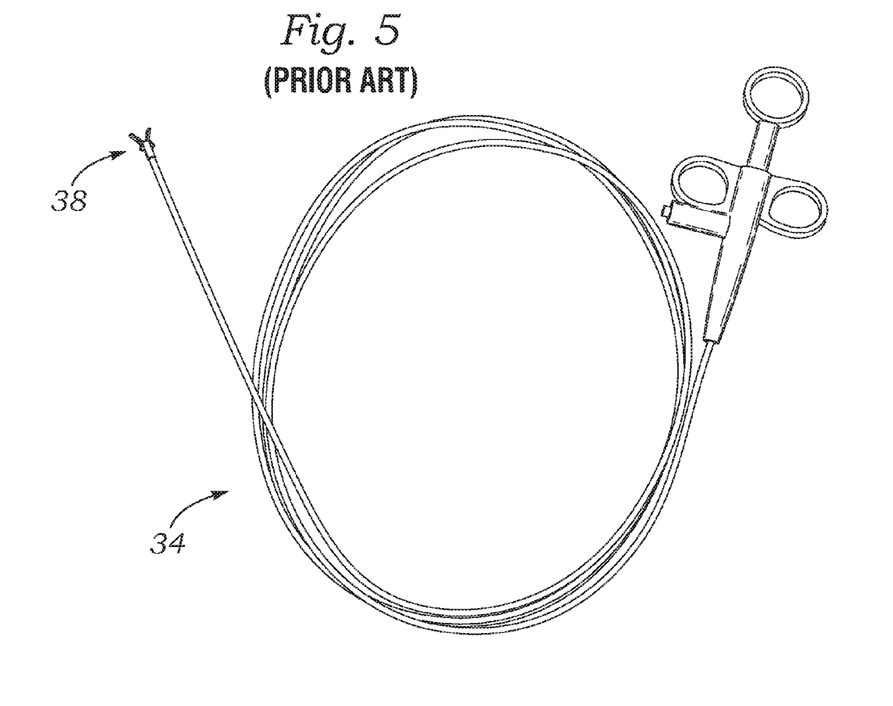
FIG. 5 shows a typical biopsy forceps in a coiled configuration.

Given that the colon is relatively long, the biopsy forceps 34 used in such procedures are thin flexible tubes (the length is typically between 2-3 m), as seen coiled in FIG. 5, which are advanced down and retracted back through the colonoscope tube 22. There are a number of different styles, with cup or teeth jaws and with or without a guide needle between the jaws, for example. One current supplier, Conmed of Utica, N.Y., offers a complete line of disposable biopsy forceps called the Precisor® Biopsy Forceps. Usually the process involves taking multiple samples, sometimes as many as 30-40 biopsies. The process of advancing the forceps 34, taking a sample, and then retracting the forceps is relatively time-consuming, and there is a need for a system that enables samples to be taken more quickly.

SUMMARY OF THE INVENTION

The present application provides a device for quickly advancing/retracting a biopsy tool (or other driven object) into position through a colonoscope or other such scope. The device includes a drive actuator, a transmission for coupling the actuator to a driven object (biopsy tool), an attachment assembly that couples the device to the endoscope, such as to a biopsy port on the endoscope, an electronic control unit, and a user interface. Preferably, the driver/biopsy tool coupling consists of a combination of gears and friction rollers.

In a preferred embodiment, the present application provides a system for performing an endoscopic procedure, comprising an endoscope, a tool displacement mechanism, and a flexible tool having an end effector for manually performing a surgical procedure. The endoscope has a proximal handle, a flexible tube that may be advanced through a patient's natural orifice until a distal end reaches a diagnostic target area, a working channel lumen from a port in the proximal handle through the flexible tube to a distal end thereof, and a scope having a lens on the distal end of the flexible tube. The tool displacement mechanism directly attaches to the port in the proximal handle of the endoscope and has a relatively small profile so as not to interfere with normal manual handling of the proximal handle. The tool displacement mechanism also includes a prime mover and a transmission. The flexible tool is sized to pass through a pathway in the tool displacement mechanism directly into the port in the proximal handle of the endoscope and into the working channel lumen. The transmission of the tool displacement mechanism converts motion generated by the prime mover to a displacement force in direct contact with the tool that drives the tool distally and proximally through the port and working channel lumen.

A method of quickly obtaining biopsies is disclosed, including the steps of: attaching a drive assist unit to an endoscope, inserting a biopsy tool into the endoscope through the drive assist unit, activating the drive assist unit through a user interface and electronic control unit to advance the biopsy tool, manually steering the biopsy tool after it emerges from a distal end of the endoscope, manually obtain a biopsy sample, and activating the drive assist unit to retract the tool and remove the sample from the biopsy tool.

DETAILED DESCRIPTION

Colonoscopy typically involves insertion of a long, flexible and steerable colonoscope via the anus to access the large intestine. An integrated camera allows visualization, and a working channel permits the use of externally actuated biopsy forceps or similar devices. One of the difficulties of the procedure, and one which leads to more time spent under anesthesia, is the need to repeatedly insert and remove the biopsy tool through the working channel when tissue samples are taken. This is tedious and taxing for the doctor (taking about 15-20 seconds and 30-35 hand/arm strokes for each insertion) and poses a risk to the patient who remains under anesthesia for longer than is fundamentally necessary. Bowel puncture is also a potential risk as the biopsy tool emerges from the end of the colonoscope, and automated insertion of the tool would allow more controlled and repeatable insertion of the tool up to the tip of the colonoscope. Automation of this tool handling process would thus improve workflow and reduce patient risk.

The present application provides an assistive device for endoscopic procedures, such as colonoscopies. The device is intended to be coupled to a conventional endoscope/colonoscope to provide more rapid advancement and retraction of a biopsy tool passed therethrough. In this respect, the biopsy tool displacement mechanism may be used to retrofit most endoscopes/colonoscopes on the market that have a working channel lumen for passage of biopsy tools. Typically such lumens terminate in a side port on a handle of the endoscope/colonoscope, but is conceivable that the lumen terminates along the axis of the handle, or in some other arrangements. Those of skill in the art will understand that the present application can be retrofitted to various such configurations.

Figure 6:
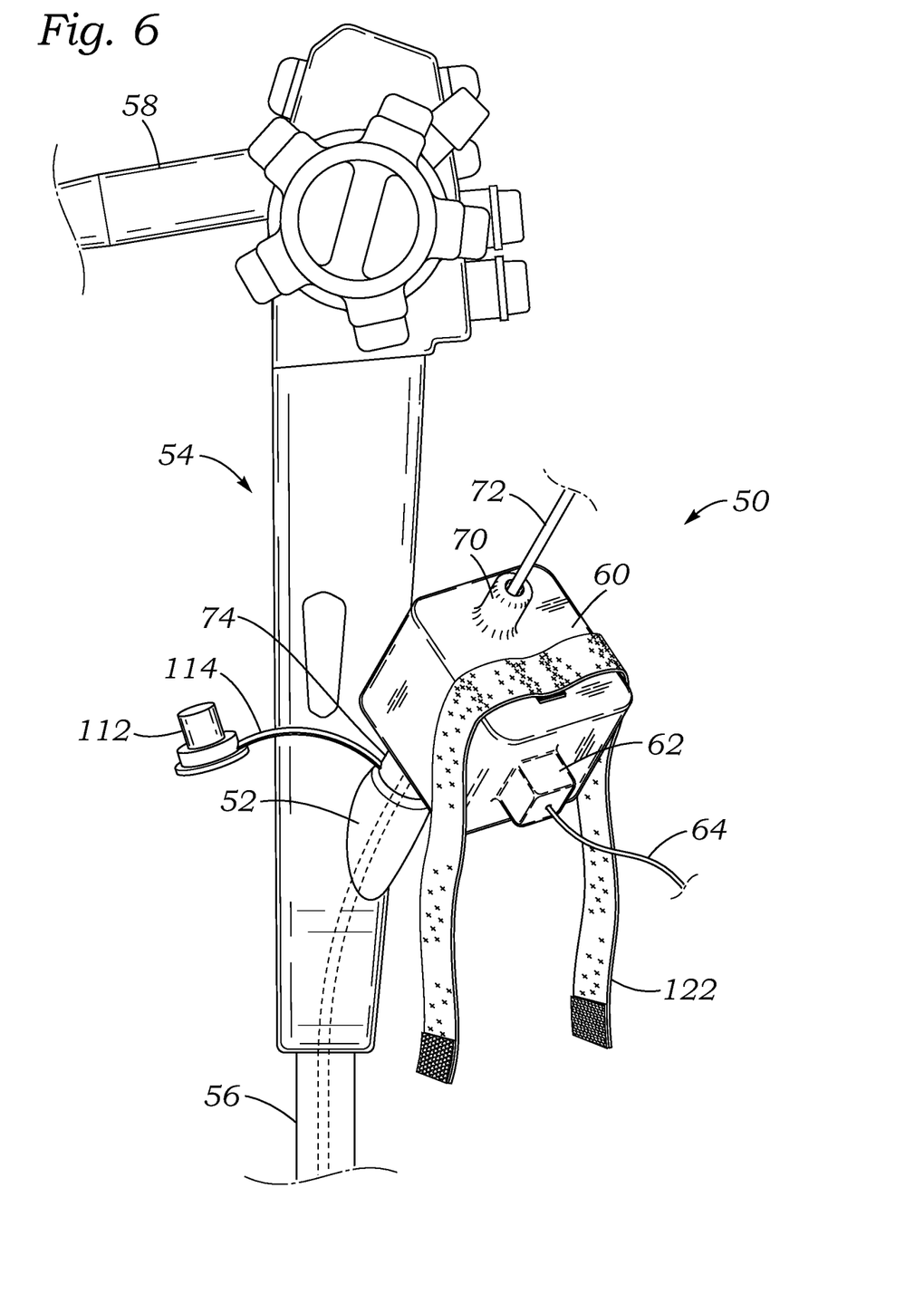
FIG. 6 is an elevational view of a colonoscope handle having an exemplary embodiment of a biopsy tool displacement mechanism coupled thereto.

FIG. 6 illustrates a biopsy tool displacement mechanism 50 coupled to a side port 52 of a colonoscope handle 54. A proximal end of a flexible tube 56 of the colonoscope is seen at the bottom, while a portion of a communication cable 58 is seen near the top. Again, the cable 58 may also provide an avenue for an air line for insufflation purposes. The functionality of the colonoscope will not be further described, and those of skill in the art will understand that various options exist, including the standard procedure described above in the background section. One exemplary colonoscope that can be retrofit with the biopsy tool displacement mechanism 50 is the Olympus CF-100TL, manufactured by the Olympus Corporation of Tokyo, Japan, available via various third-party vendors.

The biopsy tool displacement mechanism 50 comprises a generally rectilinear housing 60 having a small motor housing 62 projecting from one side. An electric cord 64 extending from the motor housing 62 provides electricity for operation of the motor, as well as communications for its actuation. For example, the cord 64 may extend to a power source via a foot switch (not shown) which is used to actuate the motor inside the housing 62 in both directions, as will be described. A control box is not shown, but may be located remotely (wherever the user wants) and desirably houses a power supply and microcontroller. A control panel or interactive display can also be located either on the control box or in a third location to provide user input to the system, telling it whether to advance, retract, or stop driving the biopsy forceps.

It should be noted that an electric motor is a desirable prime mover for use in driving the biopsy tool back and forth linearly through the flexible tube 56 of the colonoscope, though other prime movers could be used. For instance, hydraulic or pneumatic motors could serve the same function, and linear actuators could also be used if properly coupled, e.g., through a gear rack.

A small tubular member 70 extends upward from an upper side of the housing 62 and provides a port for introduction of a biopsy tool 72. The biopsy tool 72 can be seen in phantom passing downward through a lower plug member 74, into the side port 52 of the colonoscope handle 54, and then through the flexible tube 56. A central axis of the tubular member 70 at the top of the housing 62 coincides with a central axis of the lower plug member 74 so that the biopsy tool 72 extends straight through the biopsy tool displacement mechanism.

As will be explained, the displacement mechanism 50 provides a convenient assistive device to rapidly move the biopsy tool 72 through the flexible tube 56. The biopsy tool 72 has a distal end effector such as a tissue grabber as described above for sampling biopsies and the like. As shown, the tool displacement mechanism 50 directly attaches to the port 52 in the proximal handle 54 of the endoscope and has a relatively small profile so as not to interfere with normal manual handling of the proximal handle. That is, the mechanism 50 may weigh 1-2 lbs and extend out from the side of the handle 54 less than one half of the length of the handle, e.g., no more than 3-4 inches.

The present application is particularly useful for rapidly advancing and retracting a biopsy tool 72 during a colonoscopy. However, the principles disclosed herein apply also to other tools that may be shuttled back and forth within an endoscope in general. For instance, procedures such as colonoscopic snare removal of polyps or placement of endoscopic stents are also encompassed. Indeed, the present assist device applies to all endoscopic procedures which use a flexible scope with a working channel, such as a gastroscope. In general, a scope is inserted in a natural orifice, and advanced to a diagnostic target area, whereupon a secondary tool is shuttled to and from the area to perform the assigned task. The flexible biopsy tool 72 is sized to pass through a pathway (described below) in the tool displacement mechanism 50 directly into the port 52 in the proximal handle and into the working channel lumen. As will be explained, a transmission of the tool displacement mechanism 50 converts motion generated by the prime mover to a displacement force in direct contact with the tool that drives the tool distally and proximally through the port and working channel lumen.

The term, "distal end effector" will be used to encompass a tissue grabber such as shown in FIGS. 4A and 4B, as well as other tools used with a larger endoscope, such as endoscopically placed stents. Consequently, "distal end effector" is broader than a tissue sampling head, and can also refer to these other tools.

Figure 7:
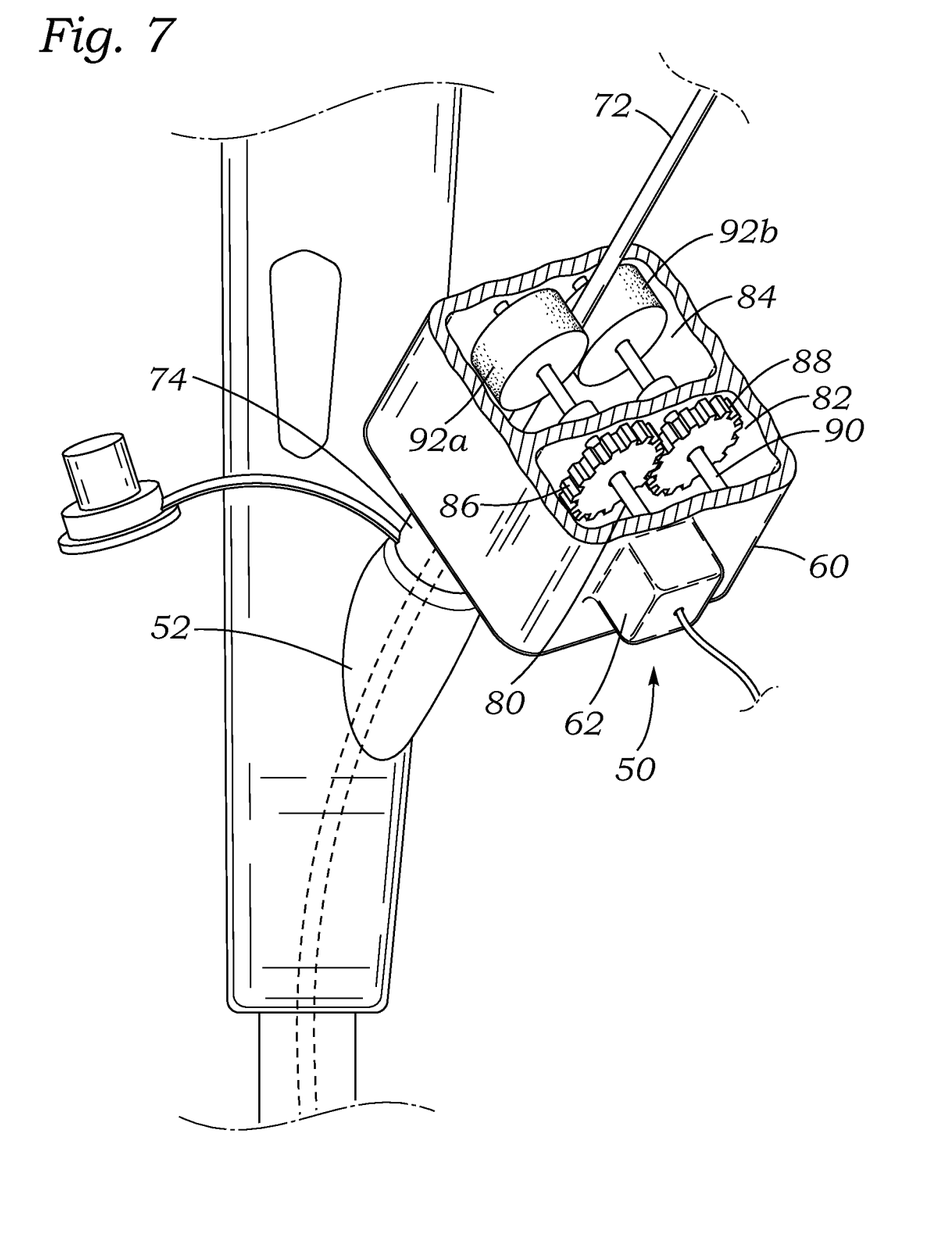
FIG. 7 is a partially cutaway view of the biopsy tool displacement mechanism.

Now with reference to FIG. 7, a partially cutaway view of the biopsy tool displacement mechanism 50 illustrates exemplary transmission and drive components therein. The motor within the housing 62 rotates a drive shaft 80 which passes through a first chamber 82 and into a second chamber 84. Within the first chamber 82, a drive gear 86 fixed to rotate with the drive shaft 80 engages a driven gear 88 keyed to rotate with a driven shaft 90. The driven shaft 90 extends parallel to the drive shaft 80, and also extends across the first and second chambers 82, 84. Rotation of the drive shaft 80 rotates the driven shaft 90 at the same speed but in the opposite direction via engagement of the gears 86, 80.

A pair of drive wheels 92a, 92b located within the second chamber 84 are mounted to rotate on the drive shaft 80 and driven shaft 90, respectively. The drive wheels 92a, 92b are preferably made of a frictional material, such as an elastomer like silicone rubber. The drive wheels 92a, 92b come into close proximity so as to frictionally engage the biopsy tool 72 therebetween, thus displacing it in a proximal or distal direction through the flexible tube 56 of the colonoscope. Actuation of the motor, therefore, displaces the biopsy tool 72 in a distal or proximal direction, depending on the direction of rotation of the motor.

Figure 8A:
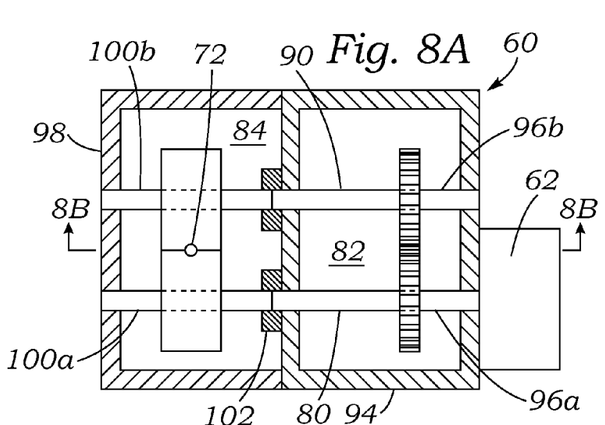
FIGS. 8A-8C are sectional views taken along orthogonal planes through the biopsy tool displacement mechanism.
Figure 8B:
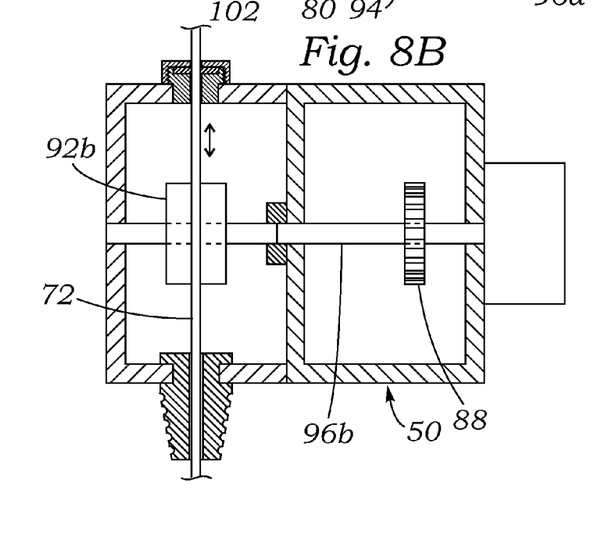
Figure 8C:
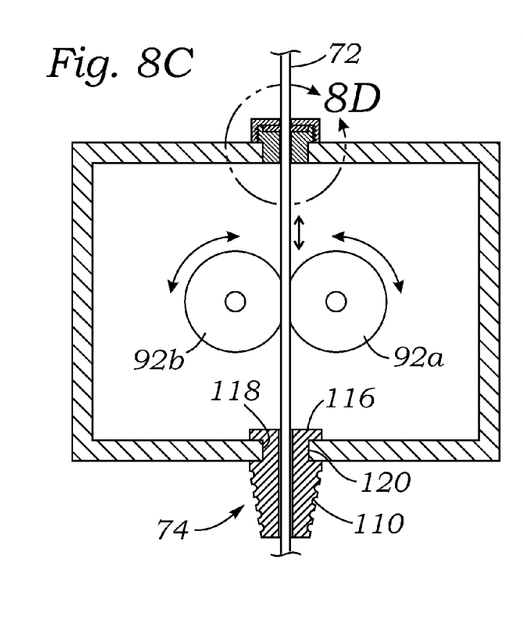

FIGS. 8A-8C are sectional views taken along orthogonal planes through an exemplary biopsy tool displacement mechanism 50. FIG. 8A is a horizontal section looking down, much like the cutaway view of FIG. 7, and shows the motor housing 62 extending from one side of the device housing 60. As explained, the drive shaft 80 extends from the motor housing 62 and across the first and second chambers 82, 84. Although the figures are somewhat schematic, it will be understood that the drive shaft 80 mounts for rotation in bearings or other such journals supported by the device housing 60. Likewise, the parallel driven shaft 90 is journalled for rotation across the first and second chambers 82, 84.

In one especially useful configuration, the device housing 60 may be segregated into two separate parts defining the first and second chambers 82, 84. As illustrated in FIG. 8A, the first chamber 82 is defined by an enclosed housing 94 within which a pair of shaft stubs 96a, 96b rotate. The first and second shaft stubs 96a, 96b project slightly through the wall of the housing 94 and into the second chamber 84. The second chamber 84 is defined by an open housing 98 which couples to the enclosed housing 94 via clips or similar expedients (not shown). A pair of shaft stubs 100a, 100b are mounted to rotate within the open housing 98 of the second chamber 84. More particularly, one end of each shaft stub 100a, 100b is supported for rotation by the housing 98, while the second end is coupled to one of the ends of the shaft stubs 96a, 96b that project into the second chamber 84. In the illustrated embodiment, annular couplers 102 are used between the respective shaft stubs 96, 100. The annular couplers 102 provide a tight interference fit between the facing ends of the shaft stubs, and suffice as torque transmitters as the level of force needed to shuttle the biopsy tool 72 is relatively small. Of course, other coupling arrangements are possible, such as sleeves locked to the shaft stubs with set screws. Simple interference fit couplers 102 are desirable for the ease of assembly and disassembly.

Providing two separable chamber housings 94, 98 enables the first chamber 82 having the motor attached thereto to be kept isolated from the biopsy tool 72, and thus free from contamination. At the end of the procedure, the open housing 98 with drive wheels 92 can be unclipped from the closed housing 94 and discarded. The closed housing 94 housing having the motor can be easily sterilized and reused, thus avoiding the expense of replacing the motor and drive transmission. The closed housing 94 defining the first chamber 82 is thus a reusable part of the biopsy tool displacement mechanism, while the second chamber 84 defining the open housing 98 is a disposable part. Moreover, the ability to switch out the housing having the drive wheels 92a, 92b enables the device to be adapted to different sizes of biopsy tool 72. For example, thicker biopsy tools 72 may require smaller drive wheels 92a, 92b, and vice versa.

With reference now to FIGS. 8B and 8C, an exemplary lower plug member 74 is shown. The plug member 74 is desirably made of elastomeric material, such as silicone rubber, and includes a tapered and ribbed lower end 110 that enables a tight fit within the side port 52 of the colonoscope handle 54. FIG. 6 illustrates a cap member 112 attached via a lanyard 114 to the side port 52. The cap member 112 fits within the side port 52 to keep out dirt and the like during periods of non-use. In this respect, the plug member 74 may be shaped like the cap member 112, which is shown as a straight cylinder, or may be tapered as seen in FIGS. 8B and 8C for a firmer attachment. The plug member 74 includes an upper flange 116 that can be forced through a lower aperture 118 in the device housing 60 such that a reduced diameter neck region 120 fits directly within the aperture. Of course, other arrangements are possible included a threaded plug. Additionally, a Velcro strap 122 as seen in FIG. 6 may be attached to the device housing 60 to further secure the biopsy tool displacement mechanism 50 to the colonoscope handle 54. The strap 122 is simply wrapped around the handle 54 and its free ends connected.

Figure 8D:
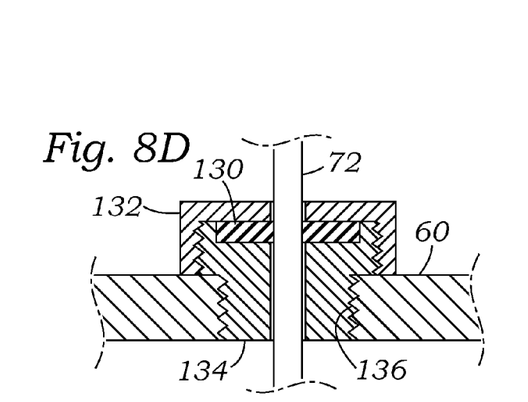
FIG. 8D is an enlargement of a wiper assembly at the top of the mechanism.

The enlargement of FIG. 8D illustrates an exemplary configuration for avoiding contamination of the colon during the procedure. Namely, an elastomeric wiper 130 in the shape of an annular washer is held firmly between an outer cap 132 and an inner ferrule 134. The ferrule 134 in turn fastens into an upper aperture 136 in the device housing 60. The ferrule 134 is shown threaded into the aperture 136, but of course a similar arrangement as described above with respect to the plug member 74 can be utilized. A through hole in the elastomeric wiper 130 is sized slightly smaller than the outer diameter of the biopsy tool 72 so as to prevent foreign matter from passing downward into the second chamber 84. This seal arrangement is believed to provide adequate sterility for the procedure while at the same time not impeding movement of the biopsy tool 72 to a great degree. In a preferred embodiment, the annular wiper 130 is made of the lubricious material such as silicone rubber or PTFE. Of course, more elaborate seals can be utilized if contamination is a greater worry.

Use of the disclosed biopsy tool displacement mechanism 50 will now be described with respect to the flowchart seen in FIG. 9. Again, the preferred method is described with respect to a colonoscopy procedure, but it will be understood by those of skill in the art that similar steps can be implemented for other endoscopic procedures. Essentially, the displacement mechanism 50 enables a physician or medical technician to rapidly shuttle an elongated tool down and back up a larger endoscope tube. In the context of a colonoscopy, the tool may be a biopsy forceps for taking tissue samples, though other tools for other applications may also benefit from being rapidly shuttled back and forth in this manner.

Figure 9:
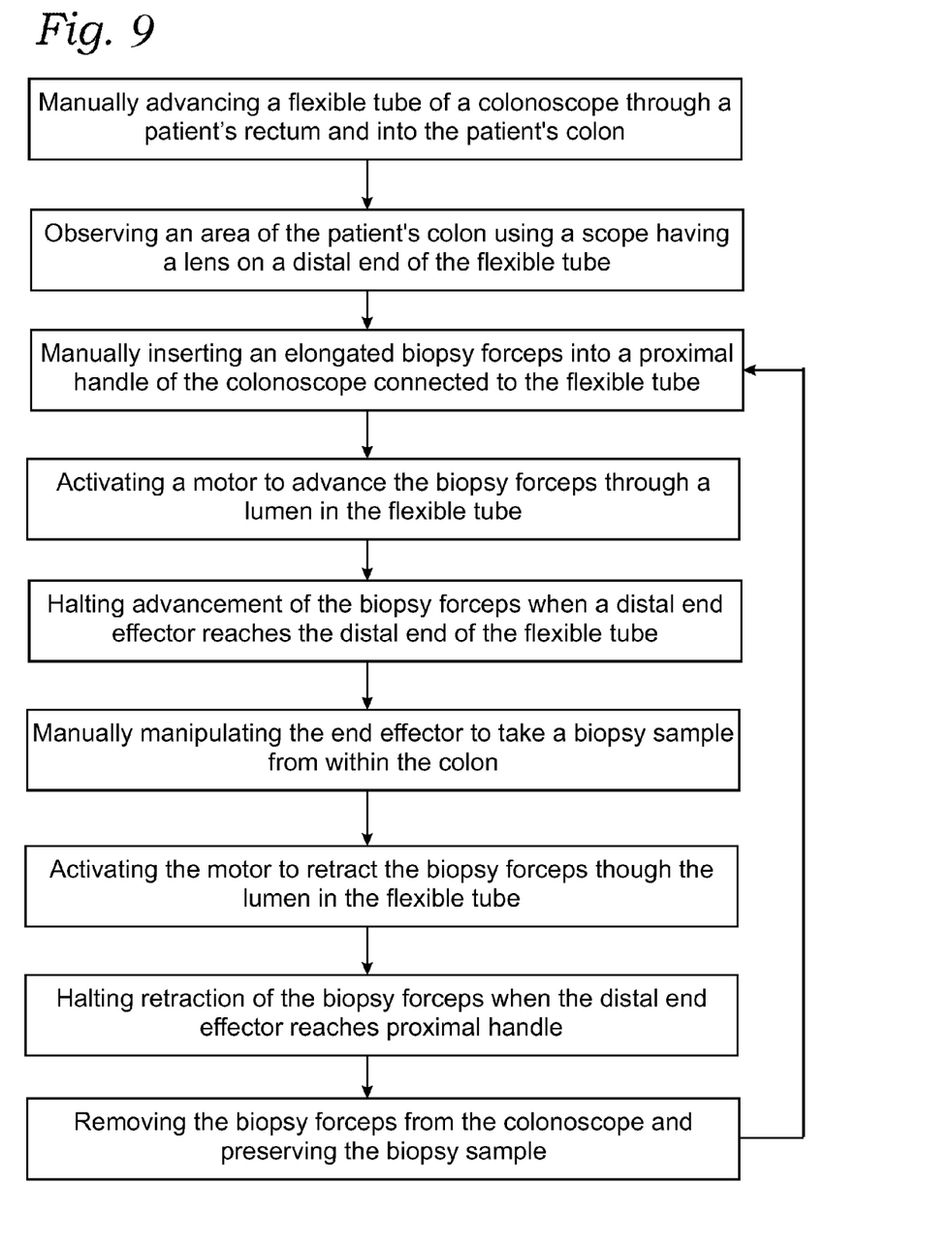
FIG. 9 is a flowchart depicting a preferred colonoscopy procedure using the biopsy tool displacement mechanism.

FIG. 9 discloses an initial step of advancing a flexible tube of a colonoscope through a patient's rectum into the patient's colon, and then observing an area within the colon using a scope having a lens on the distal end of the flexible tube. If the doctor observes an area of interest, such as a suspected polyp or tumor, he or she manually inserts an elongated biopsy forceps into a proximal handle of the colonoscope and into a lumen of the flexible tube. In order to shuttle the biopsy forceps rapidly through the flexible tube, the physician then activates a motor to displace the biopsy forceps in the distal direction at a first speed. The motor may form a part of the biopsy placement mechanism 50, as described above. As also mentioned above, the length of the biopsy forceps may be up to 3 m, and advancing the biopsy forceps using a motor greatly speeds up the process.

When the distal end effector of the biopsy forceps reaches the distal end of the flexible tube, advancement thereof is halted. This can be calibrated into the control system for the motor, such that displacement of the biopsy forceps automatically stops after a predetermined length, such as the length of the flexible tube of the colonoscope. For example, a microcontroller may be programmed to command the stepper motor for automatic advancement of the biopsy tool from insertion to near the tip of the colonoscope, with a manually driven "jog" mode thereafter for safe advancement into contact with tissue (alternatively, the tool can be advanced manually at this point by de-energizing the motor coils, and many practitioners may prefer this option). Alternatively, the physician may control advancement of the biopsy forceps through a foot pedal, or the like, and halt advancement when he or she recognizes the biopsy forceps has reached the distal end of the flexible tube. In any event, it is important to avoid expelling the biopsy forceps rapidly from the distal end of the flexible tube.

The advantage of the automatic mode comes into play more prominently during tool insertion, when the surgeon is pushing the flexible tool and it is more likely to buckle, slowing down the insertion process. Full tool advancement to the tip of the colonoscope can be achieved in approximately 3 seconds (as compared with up to 30 seconds) without risk of tissue perforation, which is a concern when advancing the biopsy instrument manually (the operator may accidentally advance the tool too far and emerge forcefully at the end of the colonoscope). The advantage of not having to slow down tool advancement at this point is not only in time savings, but also in allowing the surgeon to focus his/her mental effort on performing the diagnostic procedure rather than avoiding errors.

At this stage, the physician again manually manipulates the biopsy forceps to take a biopsy sample from within the colon. In this respect, the drive wheels 92a, 92b described above may be disengaged from contact with the biopsy forceps 72. Alternatively, the frictional forces applied to the biopsy forceps 72 by the wheels 92a, 92b may be relatively small and easy to overcome by manually pushing the forceps therethrough. In any event, the doctor has full manual control of the tissue sampling operation.

Once the tissue sample has been taken, the doctor again activates the motor to retract the biopsy forceps through the flexible tube lumen. The distance that the biopsy forceps is retracted can be calibrated so that the motor stops just when the distal end effector thereof reaches the colonoscopy handle. Alternatively, the doctor can also monitor the length of the biopsy forceps that is within the colonoscope, such as by viewing index markings along the forceps. Ultimately, the doctor removes the biopsy forceps completely out of the scope to deliver the biopsy sample so it can be placed in formalin for histologic processing and microscopic examination. The biopsy forceps can then be reinserted for additional biopsies, if needed, as shown by the feedback loop.

As explained above, a compact electromechanical device attached to a colonoscope handle speeds and facilitates biopsy tool handling in colonoscopy. As seen above, an exemplary embodiment comprises a stepper motor, friction rollers, and a structural housing. One of the friction rollers is driven directly by the motor while the other is driven with equal rotational speed in the opposite direction via a pair of gears. Alternatively, the motor could directly drive a single friction roller, with a low-friction sliding surface or passive roller opposite. This produces ideally slip-free rolling contact into which the biopsy tool can be introduced to generate linear travel of the tool with speed equal to the product of the motor speed and roller radius. The stepper motor provides a desirable combination of high driving torque to overcome friction as the tool is advanced and easy backdriving when the coils are not energized (for manual control of the biopsy tool after it is advanced beyond the tip of the colonoscope). Thus, the biopsy tool can be manually operated as usual without need for removal of the automatic advancement device. The housing provides bearing support for the shafts and encloses the gearing, and has an aperture to press-fit onto the rubber biopsy port typical to colonoscopes.

Due to concerns related to sterilization and reuse, the device was designed in two parts: a disposable section through which the biopsy tool passes, and a reusable, sealed section for the motor and gears. Since it does not come into direct contact with the soiled biopsy tool, this reusable section should only require exterior wipe-down as opposed to thorough break-down and sterilization. The two sections have interlocking mating geometries ("box" joints, visible in FIGS. 8A and 8B) such that they are easily attached/detached, and splined shaft couplers on the reusable section mate with their counterparts on the disposable section to transmit rotational motion to the rollers. The present application provides a simple device for automation of handling biopsy tools during colonoscopy procedures. Due to the simplicity of the exemplary device, it is inexpensive to produce and could provide a cost benefit in terms of reduction in procedure time, as well as improving safety. Furthermore, by significantly reducing the time and effort required for tool insertion, the device would reduce fatigue and the risk of repetitive use injury to the colonoscopist's arm and wrist. The tissue-contacting part of the device is designed to be disposable in order to facilitate the sterilization processes between procedures. Testing has indicated repeatable and reliable functionality for preventing accidental forceful excursion of the biopsy instrument beyond the tip of the colonoscope during insertion. Further testing in the presence of lubricants typically used in colonoscopy may be indicated to determine if any adjustment to surface properties of the friction rollers is necessary.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to any flowcharts if included, additional and fewer steps may be taken, and the steps as shown may be combined or further refined to achieve the methods described herein. Acts, elements and features discussed only in connection with one embodiment are not intended to be excluded from a similar role in other embodiments.

It is claimed:

1. A method of performing an endoscopic procedure, comprising:
   a) manually advancing a flexible tube of an endoscope through a patient's natural orifice until a distal end reaches a diagnostic target area;
   b) observing an area of the diagnostic target area using a scope having a lens on the distal end of the flexible tube;
   c) manually inserting an elongated flexible tool into a port of a proximal handle of the endoscope connected to the flexible tube;
   d) activating a prime mover in a tool displacement mechanism attached to the proximal handle of the endoscope to advance the tool through a working channel lumen in the flexible tube;
   e) halting advancement of the tool when a distal end effector reaches the distal end of the flexible tube;
   f) manually manipulating the end effector to perform a surgical procedure within the diagnostic target area;
   g) activating the prime mover to retract the tool through the working channel lumen in the flexible tube;
   h) halting retraction of the tool when the distal end effector reaches the proximal handle;
   i) detaching the tool displacement mechanism from the proximal handle; and
   j) separating a reusable part of the tool displacement mechanism including a prime mover from a disposable part of the tool displacement mechanism, wherein the reusable part includes an enclosed housing within which is housed the prime mover and drive components, and wherein the disposable part includes a housing that is detachably coupled to the enclosed housing and which includes driven components to advance the tool that are driven by the drive components.

2. The method of claim 1, wherein the surgical procedure is a biopsy removal wherein the end effector grabs a biopsy sample from within the diagnostic target area, and further including:
   k) performing steps d)-h) at least twice, and, after each step h) removing the biopsy sample from the end effector.

3. The method of claim 1, wherein the surgical procedure is a colonoscopy, the endoscope is a colonoscope, the natural orifice is the rectum, the diagnostic target area is the patient's colon, the tool is a biopsy forceps, and the surgical procedure is taking a biopsy sample from within the colon.

4. The method of claim 1, wherein the disposable part includes aligned ports through which the tool passes and wiper seals positioned in the aligned ports for sealing around the tool as it passes therethrough.

5. The method of claim 1, wherein the prime mover is a motor.

6. The method of claim 5, wherein the driven components include at least one frictional drive wheel in direct contact with the tool.

7. The method of claim 1, wherein the drive components include at least one shaft stub that projects from the enclosed housing, and wherein the driven components include a shaft driven by the at least one shaft stub.

8. The method of claim 1, further including
   k) connecting the reusable part of the tool displacement mechanism to a second, unused disposable part of the tool displacement mechanism for subsequent use in another surgical procedure.

9. The method of claim 1, wherein the disposable part defines the pathway through which the tool passes, and wherein the reusable part may easily be detached from the disposable part.

10. The method of claim 9, wherein the prime mover is a motor and the tool displacement mechanism comprises a transmission with meshing gears and shaft stubs in each of the reusable and disposable parts that are coupled to rotate together but are easily separated.

11. The method of claim 10, wherein the transmission includes a pair of frictional drive wheels in direct contact with the tool that are housed within the disposable part of the tool displacement mechanism.

12. The method of claim 1, wherein the tool displacement mechanism attaches to the port in the proximal handle with a strap around the proximal handle.

13. The method of claim 1, wherein the tool displacement mechanism includes a transmission that converts motion generated by the prime mover to a displacement force in direct contact with the tool that drives the tool distally and proximally through the port and working channel lumen.

14. The method of claim 13, wherein the prime mover is a motor and the transmission includes meshing gears.

15. A method of performing an endoscopic procedure, comprising:
   a) attaching a tool displacement mechanism having a prime mover to a port in a proximal handle of an endoscope, the port leading to a lumen through a flexible tube of the endoscope;
   b) manually advancing the flexible tube through a patient's natural orifice until a distal end reaches a diagnostic target area;
   c) observing an area of the diagnostic target area using a scope having a lens on a distal end of the flexible tube;
   d) mechanically advancing a flexible tool through a working channel lumen in the flexible tube using the prime mover of the tool displacement mechanism;
   e) manually performing a surgical procedure with the end effector within the diagnostic target area;
   f) mechanically retracting the tool through the working channel lumen in the flexible tube using the prime mover of the tool displacement mechanism;
   g) detaching the tool displacement mechanism from the proximal handle;
   h) separating a reusable part of the tool displacement mechanism including a prime mover from a disposable part of the tool displacement mechanism, wherein the reusable part includes an enclosed housing within which is housed the prime mover, and wherein the disposable part includes a housing that is detachably coupled to the enclosed housing and which includes aligned ports through which the tool passes and driven components that contact the tool; and
   i) connecting the reusable part of the tool displacement mechanism to a second, unused disposable part for subsequent use in another surgical procedure.

16. The method of claim 15, wherein the surgical procedure is a biopsy removal wherein the end effector grabs a biopsy sample from within the diagnostic target area, and further including:
   j) performing steps b)-f) at least twice, and after each step f), removing the biopsy sample from the end effector.

17. The method of claim 15, wherein the surgical procedure is a colonoscopy, the endoscope is a colonoscope, the natural orifice is the rectum, the diagnostic target area is the patient's colon, the tool is a biopsy forceps, and the surgical procedure is taking a biopsy sample from within the colon.

18. The method of claim 15, wherein the reusable part includes at least one shaft stub that projects from the enclosed housing, and wherein the driven components include a shaft driven by the at least one shaft stub.

19. The method of claim 15, wherein the prime mover is a motor.

20. The method of claim 19, wherein the driven components include at least one frictional drive wheel in direct contact with the tool.

21. The method of claim 15, wherein the tool displacement mechanism includes a transmission that converts motion generated by the prime mover to a displacement force in direct contact with the tool that drives the tool distally and proximally through the port and working channel lumen.

22. The method of claim 21, wherein the prime mover is a motor and the transmission includes meshing gears.

23. The method of claim 15, wherein the tool displacement mechanism attaches to the port in the proximal handle with a strap around the proximal handle.

24. The method of claim 15, further including wiper seals positioned in the aligned ports of the disposable part for sealing around the tool as it passes therethrough.

25. The method of claim 24, wherein the reusable part may easily be detached from the disposable part.

26. The method of claim 25, wherein the prime mover is a motor and the tool displacement mechanism comprises a transmission with meshing gears and shaft stubs in each of the reusable and disposable parts that are coupled to rotate together but are easily separated.

27. The method of claim 25, wherein the transmission includes a pair of frictional drive wheels in direct contact with the tool that are housed within the disposable part of the tool displacement mechanism.

28. The method of claim 15, further including
j) connecting the reusable part of the tool displacement mechanism to a second, unused disposable part of the tool displacement mechanism for subsequent use in another surgical procedure.

\* \* \* \* \*